(12) United States Patent
Ambuske et al.

(10) Patent No.: US 7,260,850 B2
(45) Date of Patent: Aug. 28, 2007

(54) BANDED GOGGLES FOR A WINTER SPORTS HELMET

(75) Inventors: Aaron Ambuske, Seattle, WA (US); Andrew Logan, Newbury Park, CA (US); Scott McManigal, Pacific Palisades, CA (US)

(73) Assignee: K-2 Corporation, Seattle, WA (US)

( * ) Notice: Subject to any disclaimer, the term of this patent is extended or adjusted under 35 U.S.C. 154(b) by 236 days.

(21) Appl. No.: 11/003,929

(22) Filed: Dec. 3, 2004

(65) Prior Publication Data

US 2005/0160522 A1 Jul. 28, 2005

Related U.S. Application Data

(60) Provisional application No. 60/527,517, filed on Dec. 5, 2003.

(51) Int. Cl.
*A42B 3/18* (2006.01)
(52) U.S. Cl. .................... 2/6.3; 2/10; 2/448
(58) Field of Classification Search ............. 2/10, 2/422, 448–450, 6.3–6.5, 6.7, 425; 351/155; 24/3.3
See application file for complete search history.

(56) References Cited

U.S. PATENT DOCUMENTS

| 2,206,997 | A | | 7/1940 | Austad |
| 2,903,700 | A | * | 9/1959 | Finken et al. .................. 2/10 |
| 3,009,158 | A | * | 11/1961 | Comeau et al. ............... 2/437 |
| 3,262,125 | A | * | 7/1966 | Bowen .......................... 2/6.7 |
| 4,141,084 | A | | 2/1979 | Krieger |
| 4,172,455 | A | | 10/1979 | Beaussant |
| 4,621,377 | A | * | 11/1986 | Pennell ......................... 2/6.4 |
| 4,686,712 | A | * | 8/1987 | Spiva ............................. 2/10 |
| RE32,638 | E | * | 4/1988 | Nesler .......................... 2/436 |
| 4,796,308 | A | * | 1/1989 | Bourgeois ...................... 2/10 |
| 4,847,920 | A | * | 7/1989 | Aileo et al. .................. 2/424 |
| 4,918,753 | A | * | 4/1990 | Mermillod .................... 2/10 |
| 5,291,880 | A | * | 3/1994 | Almovist et al. ...... 128/201.22 |
| 5,341,516 | A | * | 8/1994 | Keim ............................ 2/452 |
| 5,511,251 | A | | 4/1996 | Brakas |
| 5,809,580 | A | * | 9/1998 | Arnette ........................ 2/426 |
| 5,890,233 | A | * | 4/1999 | Kaffka ........................ 2/424 |
| 5,987,652 | A | * | 11/1999 | Fowler ........................ 2/424 |
| 6,047,410 | A | | 4/2000 | Dondero |
| 6,119,276 | A | | 9/2000 | Newcomb et al. |

(Continued)

FOREIGN PATENT DOCUMENTS

FR    2 838 333 A1    10/2003

*Primary Examiner*—Katherine Moran
(74) *Attorney, Agent, or Firm*—Christensen O'Connor Johnson Kindness PLLC

(57) ABSTRACT

Eyewear, such as goggles, includes a frame, a lens supported by the frame, and an outrigger that is pivotally mounted to sides of the frame. An elastic band is mounted to the outrigger. The elastic band is made from two band arms that are connected on one end to form a loop, and at the opposite end, the arms have loose ends, but can be attached and detached from the outrigger. The attachable and detachable aspect of the band provides the opportunity to interchange the band when the band is worn or broken, or alternatively, a completely different style of band can be used with the eyewear. For example, a traditional looking band having a stretchable elastic textile band can be substituted for the band with two arms.

5 Claims, 4 Drawing Sheets

U.S. PATENT DOCUMENTS

| | | | |
|---|---|---|---|
| 6,708,340 B1 * | 3/2004 | Dondero | 2/10 |
| 6,711,751 B1 | 3/2004 | Muskovitz | |
| 6,732,383 B2 * | 5/2004 | Cleary et al. | 2/450 |
| 6,807,679 B1 * | 10/2004 | Wang-Lee | 2/10 |
| 6,845,548 B1 * | 1/2005 | Lin | 24/265 BC |
| 6,892,393 B1 * | 5/2005 | Provost et al. | 2/10 |
| 6,952,841 B2 | 10/2005 | Schary et al. | |
| 7,062,798 B2 * | 6/2006 | Wu | 2/448 |
| 2002/0104153 A1 | 8/2002 | Benedict et al. | |
| 2003/0221246 A1 | 12/2003 | Schary et al. | |
| 2006/0117450 A1 * | 6/2006 | Matsumoto | 2/10 |

\* cited by examiner

A plurality of band types can be provided with the goggles set that are interchangeable with one another to change the look and feel of the goggles for varying situations. Additionally, a helmet and goggles set can be provided, wherein the helmet has a post on each side of the helmet that corresponds with a slot that is provided in one end of a goggles band to be mounted directly to the helmet.

BANDED GOGGLES FOR A WINTER SPORTS HELMET

CROSS REFERENCE TO RELATED APPLICATION

This application claims the benefit of provisional U.S. Application No. 60/527,517, filed Dec. 5, 2003, incorporated herein expressly by reference.

FIELD OF THE INVENTION

The invention is related to goggles and to a helmet made to be worn with the goggles.

BACKGROUND OF THE INVENTION

Conventional protective gear for winter sports typically includes a helmet and goggles. Conventional goggles have an elastic strap that encircles the back of the helmet to hold the goggles in place. The single elastic strap is attached at its ends to respective sides of the goggles. The use of a single elastic strap has its drawbacks. The goggles remain on the helmet due only to the pressure applied by the elastic strap. The goggles are otherwise not physically attached to the helmet and may be dislodged by accident. Also, if the user wants to temporarily remove the goggles, the user normally places the goggles on the helmet just above the forehead. In the forehead position, the goggles are prone to slipping and falling off the helmet.

Accordingly, there is a need to provide alternative goggles without having the aforementioned drawbacks.

SUMMARY OF THE INVENTION

The present invention is related to eyewear, such as goggles. In one embodiment, the eyewear includes a frame, a lens supported by the frame, and an outrigger that is mounted to at least one side of the frame. An elastic band is mounted to the outrigger. In one embodiment the outrigger is pivotably mounted to the frame. The elastic band may be made from two band extremities such as band arms that are connected on one end of the band to form a loop, and at the opposite end, the arms have loose ends, but can be attached and detached from the outrigger. The attachable and detachable aspect of the band provides the opportunity to interchange the band when the band is worn or broken, or alternatively, a completely different style of band can be used with the eyewear. For example, a traditional looking band having a stretchable elastic textile band can be substituted for the band with two arms.

The embodiment of the band having two arms that form a loop at one end can be attached to the helmet by providing a keyhole structure at the loop end. The keyhole structure includes a flared entrance leading to a circular slot that forms two retaining tips at the confluence of the flared entrance with the circular slot. The circular slot diameter is approximately the same diameter as a post attached to a side of a helmet. The band further includes a grip to pull the keyhole structure behind the post on the helmet. Releasing the grip allows the keyhole structure to engage the helmet post. The helmet post includes a stem and an enlarged head to prevent the release of the band from the helmet. Each side of a helmet can be provided with an elastic band attached to the goggles via an outrigger, and to the helmet via a post.

The present invention provides numerous advantages, including providing a secure method of holding the goggles to the helmet and preventing the accidental dislocation of the goggles. Furthermore, the attachable and detachable aspect of the goggles band provides for the possibility of having interchangeable bands that can be replaced when worn or torn. Alternatively, bands of a different type can be interchanged to provide for a different look and feel to the goggles. A goggles set includes goggles having a frame, a lens supported by the frame, and an outrigger.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
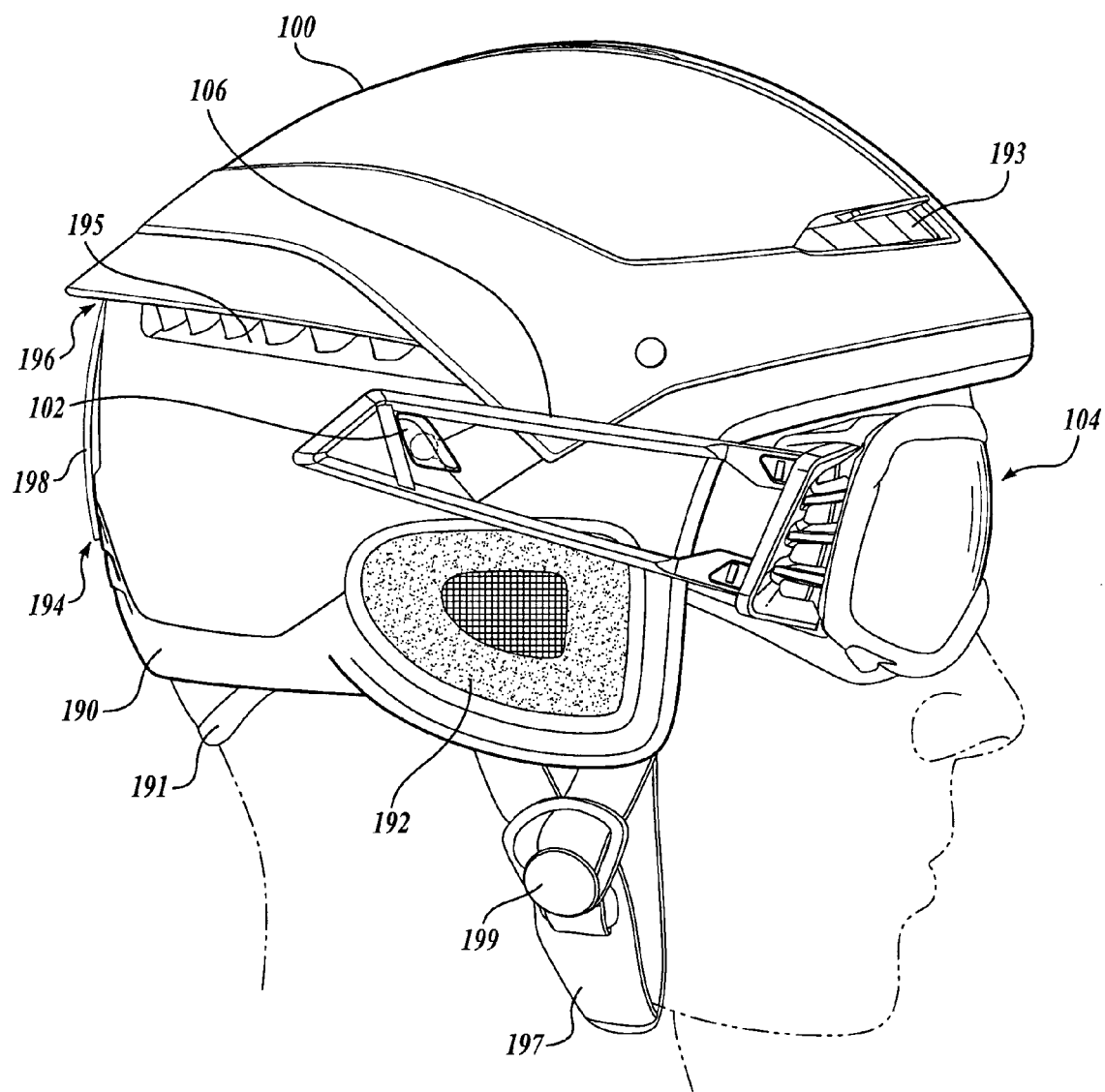
FIG. 1 is an illustration of a helmet and goggles according to the present invention.
Figure 2:
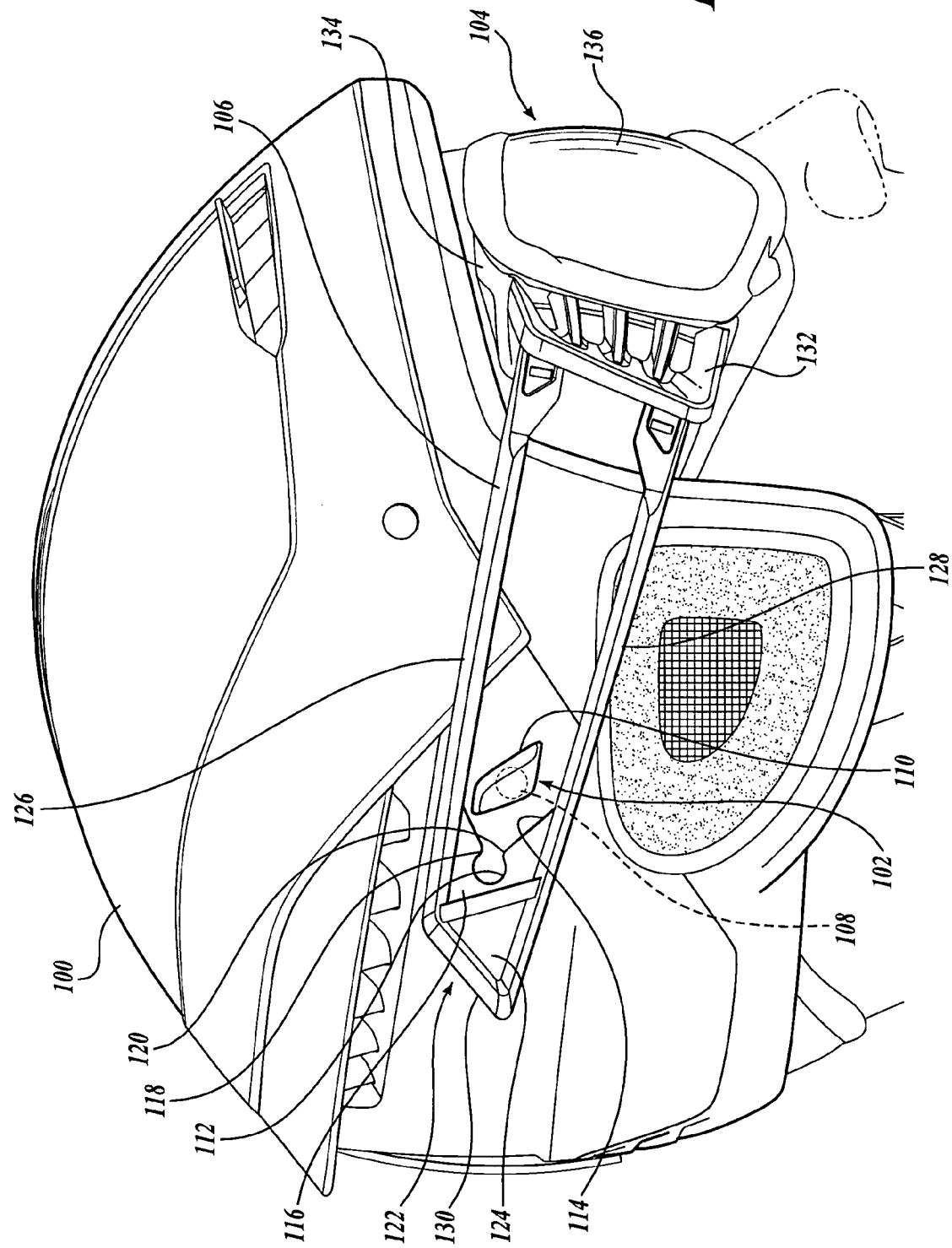
FIG. 2 is an illustration of goggles according to the present invention.

Referring to FIGS. 1 and 2, illustrations of the helmet and goggles according to the present invention, are shown.

The helmet 100 according to the present invention, includes a post 102 located on each side of the helmet 100. One embodiment of helmet 100 is more fully described in the U.S. Patent Application Publication No. US 2005/0241049 A1, filed Dec. 3, 2004, titled "HELMET WITH IN-MOLD AND POST-APPLIED HARD SHELL." This application is expressly incorporated herein by reference. Each post 102 can be located anywhere on the lateral or medial side of the helmet, but generally, each post 102 is located in proximity to the ear or the temporal area of the head. Goggles 104 are attached to the helmet 100 with an elastic band 106 on each side. The band 106 loops around each post 102 and is thereby secured to the post 102. The helmet 100 can include accessory components, such as, but not limited to ear muffs 192, plastic trim 190, interior padding 191, such as textile-covered foam and textile mesh, front 193 and rear 195 vents, chin strap 197 and chin strap buckle 199. It is to be appreciated that the opposite side of the helmet and goggles can be similarly constructed as the side shown in FIGS. 1 and 2.

As shown enlarged in FIG. 2, the post 102 comprises a stem portion 108 projecting outward from the surface of the helmet, and a head portion 110 attached to the stem portion 108. The stem portion 108 is of a diameter that will match with a corresponding circular slot 112 in one end of each band 106. Generally, a circular post is desirable to provide the goggles 104 the ability to rotate about the post 102. The head portion 110 prevents the loop end of the band 106 from pulling out and off the helmet 100. The post 102 can be affixed to the helmet 100 by a screw (not shown) bored through the center of the post 102. Alternatively, other fasteners or attachment systems can be used.

The goggles band 106 is elastic that allows the band 106 to be pulled and stretched behind the helmet post 102. Elasticity of the band 106 biases the goggles 104 snug against a user's face. The band end 122 that is attached to the post 102 includes a flattened portion 116 having the keyhole structure. The keyhole structure has a flared entrance 114 with diagonal sides leading to a circular slot 112. The slot 112 intersects the flared entrance 114 at a circle chord that is smaller than the diameter of the slot to create the keyhole structure. At the confluence of slot 112 with the flared entrance 114, a constriction is formed that creates two opposed retaining tips 118, 120. The band end 122 further includes a grip 124 that allows the user to grip the band end 122 to pull the band end 122 beyond and behind the post 102. The band end 122 can then be released or pushed onto the post 102. The flared entrance 114 guides the band end 122 onto the helmet post 102. The post 102 squeezes by the retaining tips 118, 120 before the post 102 comes to rest and is held captive in the circular slot 112. The retaining tips 118, 120 prevent the band end 122 from releasing. The goggles 104 can dangle from one post by the band end 122 being held in place by the retaining tips 118, 120. The post 102 rests snugly within the circular slot, which is dimensioned for the post diameter. Additional flattened material 116 surrounding the circular slot 112 creates an abutment against the inside surface of the post head 110 so that the band end 122 is prevented from sliding out from the post 102.

One embodiment of the goggles band 106 includes an upper and lower arm 126 and 128 that are connected to form the loop 130 at the band end 122. At the ends opposite to the loop 130, each arm is attachable and detachable to an outrigger 132. The outrigger 132 is attachable and detachable from the goggles frame 134. The frame 134 further provides support for a goggles lens 136. The band 106 may be formed from an elastomer, such as silicone, rubber, and the like.

Figure 3:
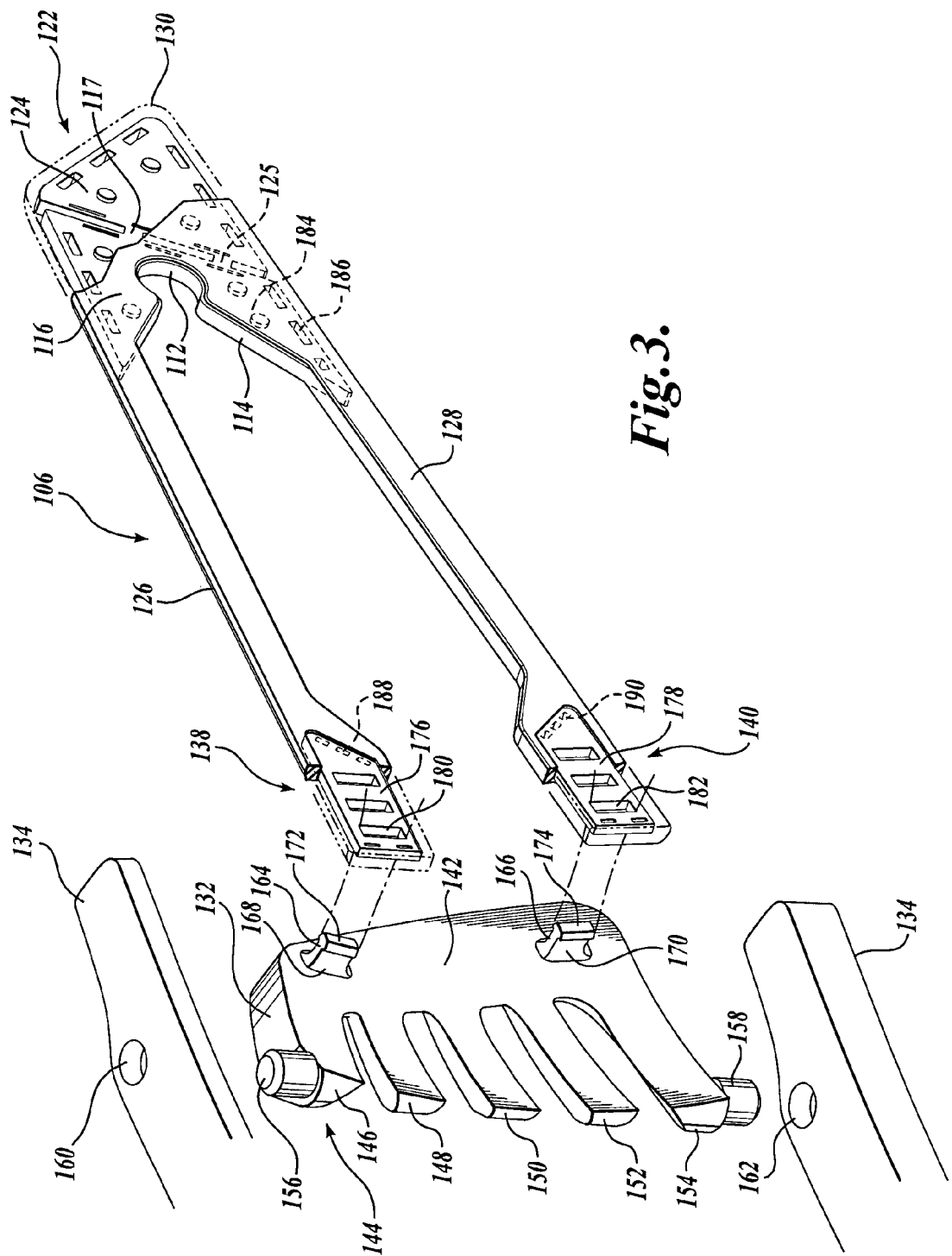
FIG. 3 is an illustration of an outrigger and an elastic band according to the present invention.

Referring additionally to FIG. 3, the outrigger 132, according to the present invention, is more clearly illustrated. Only the band of one side is being illustrated and described, however, it should be appreciated that a similar band can be provided on the opposite side of the helmet, albeit a mirror image of the one illustrated. The outrigger 132 is provided to attach the loose ends 138, 140 of the band arms 126, 128 to the goggles frame 134. As shown in FIG. 3, the outrigger 132 includes a first 142 and second 144 major surface, wherein surface 142 is slightly concave and the surface 144 is slightly convex. The concave surface 142 faces the user, the convex surface 144 faces outward. Prongs 146, 148, 150, 152, and 154 extend parallel to the major surfaces 142, 144. At least one flexible prong is disposed at the exteriormost upper or lower side of the outrigger 132. "Flexible" means a prong can be depressed, at a minimum, in the direction toward the center prong 150 of the outrigger 132. Each exteriormost prong 146 and 154 includes a small rounded peg 156, 158 or "pintle" pointed in the direction parallel to the outrigger major surfaces. The pintles 156, 158 are aligned with each other and sized to fit into a corresponding gudgeon 160, 162 or socket on the frame 134 of the goggles 104. The prongs 148, 150 and 152 are not necessary, however, these prongs can be provided to increase the ventilation around the face area. One or both of the prongs 146, 154 can be depressed slightly toward the center prong 150 so as to be able to fit the outrigger 132 between opposed gudgeons 160, 162. In this manner, the outrigger 132 is attachable and detachable from the goggles frame 134. When the pressure on the prongs 146, 154 is released, the prongs 146 and 154 will return to their original position and the pintles 156, 158 will fit into the corresponding gudgeons 160, 162 on the upper and lower sides of the frame 134. The use of rounded pintles is advantageous since the outrigger 132 can pivot about the pintles.

The concave major surface 142, has a first and second barb 164, 166 that extend generally perpendicular to the major surface 142. Each barb 164, 166 includes a stem portion 168, 170 and an enlarged head portion 172, 174. When viewed through a cross-section parallel to the major surfaces, the barb stems 168, 170 and barb heads 172, 174 may be generally rectangular. The head portions 172, 174 may be slightly greater in area and form a downward sloping chamfer, which facilitates insertion of band ends 138, 140 but makes the removal of the band ends 138, 140 more difficult. Other configurations of outrigger barbs are possible, such as rounded pegs with "mushroom" heads. Alternatively, other types of fasteners that can be used to attach the outrigger to the band ends 138, 140 are possible. The outrigger 132 can be made of a rigid plastic material, such as a polyamide. As used in this application, "nylon" is the generic designation for all synthetic polyamides.

Referring to FIG. 3 in conjunction with FIG. 2, the band arms 126, 128 are connected in a loop 130 at the band end 122 that is attachable and detachable to the helmet post 102, but are unconnected to each other at the forward, opposite ends 138, 140. However, band ends 138, 140 are attachable and detachable to the outrigger 132 via barbs 164, 166. In one embodiment, each arm end 138, 140 may include a flattened arm end plate 176, 178 with a plurality of holes aligned sequentially therein, wherein holes 180, 182 are representative of each end 138, 140. The holes, such as holes 180, 182, are rectangular and sized to fit into the outrigger barbs 164, 166 to adjust the length of the band arm that is attached between the outrigger 132 and helmet post 102. At the loop end 122, the band arms 126, 128 form the loop 130 that is attached to flat portion 116 with the keyhole structure, and grip 124, described above. As shown in FIG. 3, a rigid flat plate material 184 may form both the keyhole structure and grip. In FIG. 3, the three band plate components 184, 176 and 178 may be made of a rigid non-elastic, material, such as nylon, that is different from the elastomeric material from which the bands are made.

As shown in FIG. 3, the two small plates 176 and 178 may be made to be joined to the respective arm ends 138, 140. Each plate 176, 178 is encased on its four side edges by the elastic material thusly holding the plates 176, 178 securely in place to the arm ends 138, 140. However, the elastic material does not cover the holes, such as 180, 182, to enable the insertion of barbs 164, 166 therethrough. The third plate component 184 includes the keyhole structure and grip 124 that is located at the loop end 122 of band 106. As discussed above, the keyhole structure is shaped from flat area 116 including circular slot 112 and flared entrance 114 that are joined at a confluence to produce retaining tips 118, 120. Grip 124 is provided in the shape of a triangle, however, any other suitable shape is possible. Grip 124 and flat area 116 are connected by small areas of material 117, 125 bridging grip 124 and flat area 116 to provide some amount of flexibility to grip 124. Component 184 is encased by elastic material on three side edges, and optionally on one or both major surfaces. The edge on the side of flared entrance 114 is not encased to enable the insertion of helmet post 102. Each of the three rigid band components 184, 176 and 178 can be provided with small holes, such as 186 188 and 190, along the perimeter edges so that the elastomeric material will fill in the holes 186, 188, and 190, and securely hold the rigid components 184, 176, and 178 to the elastomeric material. The components 184, 176 and 178 can be cast in place with the elastomeric band 106. Rigid materials include nylon; however, other materials can be used, including metals.

Referring momentarily to FIG. 2, the goggles 104 include a lens portion 136. The lens portion 136 is surrounded by the frame 134. The frame 134 has a pair of gudgeons, such as 160, 162 shown in FIG. 3, on each side of the goggles frame 134 to receive the outrigger pintles 156, 152 shown in FIG. 2. Additionally, the goggles 104 may have open or closed cell foam or other material on the inside perimeter of the frame 134, or in other areas, to provide comfort, to seal around the user's face, or to provide ventilation.

Figure 4:
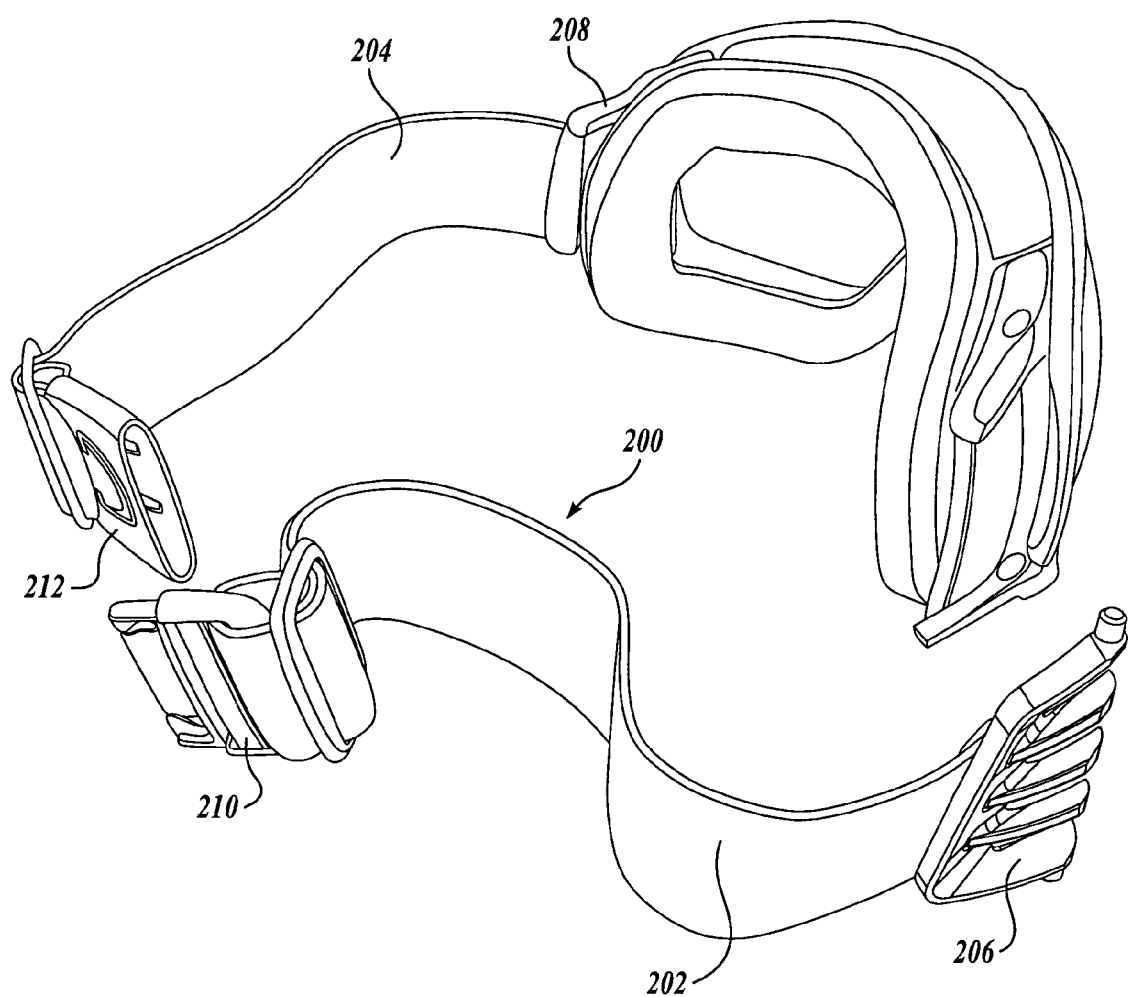
FIG. 4 is an illustration of an outrigger integrated with a woven stretchable band according to the present invention.

Referring now to FIG. 4, an alternative band 200 for the goggles according to the present invention, is illustrated. The band 200 is divided into a first and second band portion 202, 204. Each band portion 202 and 204 has an outrigger 206, 208 attached thereto to one end, and a respective buckle fastener portion 210, 212 attached at the opposite end. Alternatively, a single continuous band can be used. In this embodiment, each outrigger 206, 208 is integrated with each band portion 202, 204. Band portion 202 is attached to band portion 204 through the buckle fastener portions 210, 212 to form a band 200 that encircles the back of the helmet 100. The band portions 202, 204 can be attached to each respective outrigger by seizing the band portions to the outrigger. The buckle fasteners 210, 212 can adjust the length of the band portions between the buckle fastener and the outrigger. Alternatively, the bands 202, 204 can be nonadjustable. The bands 202, 204 can include elastic strings interwoven into a synthetic or natural fabric material, which will result in a stretchable, elastic band. Unlike the previous embodiment that did not completely encircle the head, the band 200 encircles the back of the head and/or helmet, and gives the look and feel of traditional goggles. To retain the band 200 on the back of the helmet 100, a prong 198 is attached to the back or occipital area of the helmet 100 as shown in FIG. 1. Only end 196 of the prong 198 is attached to the helmet 100. The non-attached end 194 exerts a slight pressure against the helmet 100. The band 200 can be slipped under the non-attached end 194 to secure the band 200 on the helmet 100. The band 200 can be slipped under the non-attached end 198 to secure the band 200 on the helmet 100.

According to the present invention, the helmet 100 and goggles 104 can be provided, each as a separate unit, or as a set. Furthermore, a goggles set can be provided to include the goggles having a lens and frame, an outrigger, and also including a plurality of interchangeable band types. The outrigger can be detachable from the frame, and the various goggle bands can be interchangeable with each other. For example, the set may include the goggle band having two arm loose ends and a loop at the opposite end, and the goggle band with two flat wide woven band portions connectable via a buckle. Each band type is attachable and detachable to a common outrigger which is also attachable and detachable from the goggles frame. The goggles can, for example, be used with the band that includes a loop end and two loose ends. However, if the traditional type of goggles securement is desired, the two arm ends can be detached from the outrigger, and a woven stretchable band can be attached to the outrigger to provide a traditional type goggle band. Alternatively, other types of goggle bands can be envisioned that are detachable from the outrigger to provide various selections for the user.

The goggles, goggle bands, and helmet, according to the present invention, provide the ability of the goggles to be temporarily removed and placed over the forehead part of the helmet, without the fear of the goggles slipping off of the helmet or being dislodged. Furthermore, goggle bands that are detachable from the goggles frame allows for the quick interchange of different type bands or if the need arises, worn or broken bands can be removed and replaced with newer bands without the need of discarding the entire goggles.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. Goggles, comprising:
    a frame;
    a lens supported by the frame;
    an outrigger mounted to a side of the frame; and
    an elastic band attached to the outrigger, the outrigger pivotably mounted to the frame, wherein the band comprises at least one arm attached to the outrigger, and each arm has a plurality of holes that determine the attached length of each arm.

2. Goggles, comprising:
    a frame;
    a lens supported by the frame;
    an outrigger mounted to a side of the frame; and
    an elastic band attached to the outrigger, the outrigger pivotably mounted to the frame, wherein the band comprises a first and second extremity that are connected in a loop, and the loop includes a grip and a connection structure.

3. Goggles, comprising:
    a frame;
    a lens supported by the frame;
    an outrigger mounted to a side of the frame; and
    an elastic band attached to the outrigger, the outrigger pivotably mounted to the frame, wherein the band comprises a first and second extremity that are connected in a loop, and a non-elastic plate having a keyhole structure and grip is attached at the loop.

4. Goggles, comprising:
    a frame;
    a lens supported by the frame;
    an outrigger mounted to a side of the frame; and
    an elastic band attached to the outrigger, the outrigger pivotably mounted to the frame, wherein the band comprises a first and second arm end attached to the outrigger, each arm end has a plurality of holes, the holes are formed on a non-elastic plate, and the plate is attached to each arm end.

5. A helmet and goggles set, comprising:
    a helmet having at least one post on the temporal area of the helmet; and
    goggles comprising a frame, a lens supported by the frame, an outrigger attached to a side of the frame; and
    an elastic band attached to the outrigger, the outrigger pivotably attached to the frame, wherein the band comprises a slot that is sized to mate with the post on the helmet.

* * * * *